(12) United States Patent
Orlov et al.

(10) Patent No.: US 9,494,533 B2
(45) Date of Patent: Nov. 15, 2016

(54) OPTICAL QUALITY CONTROL DEVICE

(71) Applicant: Scientific Visual SA, Lausanne (CH)

(72) Inventors: Ivan Orlov, Lausanne (CH); Yury Kuzminykh, Chavannes-près-Renens (CH)

(73) Assignee: Scientific Visual SA, Lausanne (CH)

( * ) Notice: Subject to any disclaimer, the term of this patent is extended or adjusted under 35 U.S.C. 154(b) by 16 days.

(21) Appl. No.: 14/438,852

(22) PCT Filed: Oct. 29, 2013

(86) PCT No.: PCT/IB2013/059751
§ 371 (c)(1),
(2) Date: Apr. 27, 2015

(87) PCT Pub. No.: WO2014/068479
PCT Pub. Date: May 8, 2014

(65) Prior Publication Data
US 2015/0293038 A1    Oct. 15, 2015

(30) Foreign Application Priority Data
Oct. 29, 2012  (EP) .................................... 12190469

(51) Int. Cl.
*G01N 21/00* (2006.01)
*G01N 21/95* (2006.01)
(Continued)

(52) U.S. Cl.
CPC ............ *G01N 21/958* (2013.01); *G01N 21/87* (2013.01); *G01N 21/00* (2013.01); *G01N 21/88* (2013.01); *G01N 21/95* (2013.01); *G01N 2201/06113* (2013.01)

(58) Field of Classification Search
CPC ............................ G01N 21/87; G01N 21/958
See application file for complete search history.

(56) References Cited

U.S. PATENT DOCUMENTS 3,586,444 A * 6/1971 Sproul .................. G02B 27/54
                                                    356/129
4,049,350 A * 9/1977 Bruck .................... G01N 21/88
                                                    356/239.1
(Continued)

FOREIGN PATENT DOCUMENTS

BE         1017316 A7      6/2008
WO    WO 2006/108137 A2   10/2006

OTHER PUBLICATIONS

International Search Report and Written Opinion issued by the European Patent Office, Rijswijk, Netherlands, dated Apr. 9, 2014, for International Application No. PCT/IB2013/059751; 13 pages.

*Primary Examiner* — Kara E Geisel
*Assistant Examiner* — Jarreas C Underwood
(74) *Attorney, Agent, or Firm* — Faegre Baker Daniels LLP

(57) ABSTRACT

Optical quality control system for controlling the quality of a high refractive index solid (2), comprising a container (4) configured to receive the solid therein, a structured light source (30), an optical inspection zone configured for receiving an optical device (10) or an eye of a human observer, and a high refractive index liquid (12) for insertion in the container in a volume sufficient to fully immerse the translucent solid. The structured light source is configured to project a planar light fan (20) through the high refractive index solid immersed in the high refractive index liquid generating a illuminated cross-section (18) in the solid. The optical inspection zone is arranged at a top end of the container adapted for inspection of the illuminated cross-section in a direction transverse to a plane (P) defined by the planar illuminated cross-section.

38 Claims, 10 Drawing Sheets

(51) Int. Cl.
  *G01N 21/88* (2006.01)
  *G01N 21/958* (2006.01)
  *G01N 21/87* (2006.01)

(56) References Cited

U.S. PATENT DOCUMENTS

| | | | |
|---|---|---|---|
| 4,645,337 A * | 2/1987 | Obenreder | G01N 21/958 356/128 |
| 7,307,714 B2 * | 12/2007 | Cyr | G01N 21/958 356/237.1 |
| 7,633,048 B2 * | 12/2009 | Doran | G01N 21/4795 250/221 |
| 8,098,368 B2 * | 1/2012 | Shlezinger | G01N 21/87 356/30 |
| 8,284,483 B2 * | 10/2012 | Beaurepaire | G02B 21/0048 356/141.4 |
| 8,427,656 B2 * | 4/2013 | Hullin | G01B 11/2504 356/601 |
| 2005/0259247 A1 | 11/2005 | Cyr et al. | |
| 2008/0068587 A1 * | 3/2008 | Kawasaki | G01N 21/958 356/36 |
| 2008/0231833 A1 | 9/2008 | Shlezinger et al. | |

* cited by examiner

OPTICAL QUALITY CONTROL DEVICE

BACKGROUND OF THE DISCLOSURE

The present invention relates to an optical quality control system for controlling the quality of a high refractive index translucent or transparent solid. The invention may in particular be used for controlling the quality of gemstones, sapphires, sapphire ingots, technical optical materials and crystals.

An apparatus and method for inspecting a precious stone, which is at least partially translucent, is known from U.S. Pat. No. 4,049,350. The stone is immersed in a liquid having the same or a similar refractive index. Thereafter it is scanned with a focused laser beam emitted from a laser source, and a photosensitive device comprising photoconductive cells is mounted within a plate, which is configured to carry the stone. The photosensitive device is arranged opposite of and in-line with the laser beam. Since the laser beam only allows a punctual control of the precious stone it is suggested to move the laser source and the precious stone relative to one another during the controlling operation. For this reason a motor configured to rotate the plate so that the precious stone may be rotated and a mechanism to move the laser source are provided, thus creating a spiral scanning trajectory. The laser beam is preferably moved across the stone via a pivotable mirror. Since it is preferred that the precious stone is fully immersed in a liquid having a similar refractive index as the stone, the angle of refraction of the light beam is low when it enters the precious stone and thus it passes through the stone without losing much intensity. On the other hand when the laser beam hits a bubble or inclusion it is dispersed and the intensity of the laser light passing straight through the stone will be reduced. This reduction is measured by the photosensitive device.

The high refractive index liquid reduces the reflection from the outer surfaces of the stone and the refractive bending and separation of the light when it enters the precious stone.

The device described in U.S. Pat. No. 4,049,350 does not allow determining the exact spatial position of the defect with one scan, since only the x-, and y-coordinates (horizontal) of the defect can be determined and not the z-coordinate (vertical). It is thus suggested to scan the precious stone a second time in a different direction. A second scan also allows determining whether or not a possible detected defect has its origin in a particle in the liquid or on the surface of the precious stone.

The above described process is slow and costly in view of the three dimensional point scanning process. Further, due to the nature of the method comprising a spiral trajectory of the laser beam, certain areas within the precious stone may be missed when a scan is made. Moreover, the photosensitive device is exposed and arranged within the liquid, which is potentially chemically aggressive. In case there is a problem with the photosensitive device the reparation may be costly and complex.

SUMMARY OF THE DISCLOSURE

An object of this invention is to provide an optical quality control system which enables a rapid and accurate quality control of a high refractive index translucent solid.

It is advantageous to provide an optical quality control system which is economical and easy to use.

It is advantageous to provide an optical quality control system which allows determining the exact spatial positions of defects within the high refractive index translucent solid in an economical and reliable manner.

It is advantageous to provide an optical quality control device, which is simple to operate and easy to maintain.

Disclosed herein is an optical quality control system for detecting a defect in a high refractive index translucent or transparent solid. The optical quality control system comprising a container configured to receive the solid therein. The optical quality control system further comprises a structured light source or multiple structured light sources, an optical inspection zone configured for receiving an optical inspection device or an eye of a human observer, and a high refractive index liquid for insertion in the container in a volume sufficient to fully or at least partially immerse the solid. The structured light source is configured to project a planar light fan through the high refractive index translucent solid fully or at least partially immersed in the high refractive index liquid generating an illuminated cross-section in the solid. The optical inspection zone may be arranged at an end of the container, which we shall refer to as a first end or top end, adapted for inspection of the illuminated cross-section in a direction transverse to a plane defined by the planar illuminated cross-section. The meaning of "top" and "bottom" as used herein is not intended to be limited to a position with respect the vertical direction, for example the first end may be arranged on a side of the container, rather these terms are meant to identify opposing ends of the container along the inspection direction.

It will be appreciated that the solid may be fully or partially immersed in the high refractive index liquid. Partial immersion may be achieved by allowing part of the solid to protrude from the liquid.

For example, the solid may be partially immersed such that the high refractive index liquid may immerse a side or region of the solid through which the light fan propagates. The high refractive index liquid may alternatively or additionally be partially immersed such that the high refractive index liquid immerses a side or region of the solid between the optical inspection zone and solid. Moreover, the region of the solid though which the light fan propagates into the solid may not be immersed with the region of the solid between the optical inspection zone and solid being immersed. It will be appreciated that for such examples the orientation of the inspection zone and structured light source (s) is selected accordingly.

The high refractive index liquid may be referred to more generally as a high refractive index medium. For example, it may comprise a liquid that can be poured into the container to at least partially surround the solid, the liquid being configured to be able to solidify. For example, the high refractive index medium may be adapted such that it can be heated to enable it to be poured as a liquid and then cooled such that it solidifies. It may also be adapted such that it solidifies with the application of a solidification agent, for example the high refractive index medium may be polymerised like and epoxy or polymer. The high refractive index medium may encompass a high viscosity liquid such as a gel.

The illuminated cross-section is generated when the planar light fan is projected through the high refractive index translucent solid. The planar light fan is configured to "cut" or extend through the high refractive index translucent solid. As the planar light fan is configured to cover the whole cross-section of the solid the optical quality control system allows a systematic and fast inspection. If there is no defect the light propagates undisturbed and may thus not be registered by the camera or observer's eye. If there is a defect in the high refractive index translucent solid, the light beams of the planar light fan are dispersed and the defect becomes visible to the optical inspection device or the eye of a human observer.

It is advantageous to combine a planar light fan that covers the cross section with a high refractive index solid immersed in a high refractive index medium. This is because the medium has the effect of ensuring the light fan is propagated into the solid uniformly and substantially un-refracted and un-scattered by the solid/medium interface.

In an advantageous embodiment the optical inspection system comprises a light source transport system configured to enable the light source to be displaced along the container.

Advantageously the optical inspection device may comprise a connecting portion configured to fixedly connect the optical inspection device to the structured light source or the light source transport system so that the optical inspection device may be displaced, in a direction perpendicular to the plane defined by the planar illuminated cross-section, by the light source transport system.

The refractive index of the high refractive index medium should preferably be close to, or even match, the refractive index of the high refractive index translucent solid in order to reduce the reflection from the outer surfaces of the solid and the refractive bending and separation of the light when it enters the high refractive index translucent solid.

However, there are situations where it may be of advantage when the refractive index of the high refractive index medium differs from the refractive index of the high refractive index translucent solid.

For many applications, the refractive index of the high refractive index medium is preferably in the range of 80% to 105% of the refractive index of the translucent solid, more preferably in the range of 85% to 100% of the refractive index of the translucent solid.

High refractive index mediums with a very high refractive index are very expensive. Further, if the high refractive index medium is too close to or even matches the high refractive index of the high refractive index translucent solid, the solid may be hard to observe or even to locate in the medium. In general the high refractive index of the high refractive index medium is a compromise between the quality of the inspection and cost, meaning that the lowest acceptable refractive index for the high refractive index medium is chosen. However there may be situations where a special high refractive index medium with a very high refractive index may be chosen.

The high refractive index (n) of the high refractive index medium may for many applications be in the range of 1.65 to 2.5.

For use with sapphire, which has a refractive index about 1.75-1.79 in the visible range, it is preferred that refractive index of the medium is about 1.6-1.8.

In a particular example, wherein a sapphire has a refractive index of 1.76, it is preferable that the refractive index of the medium is about 1.72. In certain applications it is advantageous to have a medium with a refractive index slightly different to that of the solid, for instance, in the range of 1-10% higher or lower, but preferably lower, to facilitate the visualisation or identification of the outer contour or the solid being inspected.

The structured light source is configured so that the planar light fan has a thickness of less than the required resolution in the inspection direction (typically less than 1 mm). For example, the light fan may be considered a sheet of light. It is desirable that the illuminated cross-section has a narrow thickness as this enables the position of a defect along a line perpendicular to the plane of the illuminated cross section to be determined precisely.

The structured light source may be configured to generate coherent light or incoherent light. In a preferred embodiment, the structured light source is a monochromatic light source.

In an embodiment, the planar light fan may comprise a plurality of light beams that propagate in different directions which are aligned to the plane (P). In a preferred embodiment the light beams diverge when viewed in the inspection direction and are aligned in the plane (P).

In a preferred embodiment the structured light source is arranged such that the planar light fan illuminates at least the entire cross-section of the solid. The cross-section may be considered a 2D cross section since it is particularly thin. In this way an entire 2D cross-section of the solid can be observed in the inspection direction at a given moment in time. One of the advantages is that the human brain can effectively evaluate a single 2D image, but cannot as effectively evaluate the same information if distributed in time, for example via a line-by-line or a point-by-point scanning technique. Moreover, it allows use of standard imaging equipment such as cameras/2D detector arrays, contrary to line-by-line or point-by-point scanning.

The illuminated cross-section is preferably arranged to extend along a plane which is substantially perpendicular to the inspection direction. Advantageously, a thin strip of the cross-section is illuminated for inspection. The thin strip can then be displaced in the inspection direction to thereby sequentially illuminate all of the volume of the solid.

In a preferred embodiment there are a plurality of structured light sources, for example there may be 2 or 3 or 4. Each of the plurality of light sources may be arranged to project a planar light fan at different angles along the plane (P). The light sources may be disposed about a central axis of the solid which may be aligned to the inspection direction. The light sources may be circumferentially arranged such that they are and equal distance away from the central axis, or may be approximately aligned with the circumferential line. In a preferred embodiment, there are 3 structured light sources, which are disposed about the central axis, for instance spaced apart from each other at 100° to 140°.

It is advantageous to have more than one structured light source which is arranged to project a light at a different angle. This is because certain defects are only visible when exposed to light within a narrow range of angles. An example of such a defect is a planar or linear crack which is aligned to the light traveling in its proximity. Another example is a second defect which can be hidden behind a first defect. Other examples of imperfections are pinpoint inclusions, or a set of pinpoints known as a cloud.

Preferably, the or each structured light source are operable to move relative the solid parallel to the inspection direction. In this way the illuminated cross section is moved through the solid so that the entire volume of the solid is sequentially illuminated. Such an arrangement may be achieved by fixing a position of the solid and moving the structured light sources or be fixing a position of the structured light sources and moving the solid.

The optical quality control device may comprise a plurality of lenses, wherein one or more of the lenses is arranged to receive light, preferably part of a planar light fan, the lenses being configured to project the received light through the solid as planar light fans projecting along the plane (P) at different angles to that of the received planar light fan. Advantageously, the lenses increase the number of directions that the light extends thought the illuminated cross-section such that the defects are more likely to be identified. The lenses may be connected to a periphery of the container or a movable element.

In an advantageous embodiment the optical inspection zone is adapted for inspection of the illuminated cross-section in an inspection direction essentially orthogonal to the plane of the illuminated cross-section.

Advantageously, the structured light source comprises a laser generating the planar light fan. The planar light fan is thus a planar laser light fan. The energy of the laser allows generating well visible illuminated cross-sections of the high refractive index translucent solid.

In an advantageous embodiment the light source transport system is configured to transport the structured light source along an inspection direction, which may form the vertical direction, from a first end of the container to a second end so that the whole high refractive index translucent solid can be scanned by the planar light fan.

The light source transport system may move the structured light source in the inspection direction so that the optical inspection device or the human eye of the observer may inspect the entire high refractive index translucent solid. The light source transport system can also move automatically with a constant speed or make step-by-step movements and/or stop for image registration.

In another advantageous embodiment the container comprises a light absorbing surface portion arranged opposite the light source configured to reduce reflection of light within the container.

A light absorbing surface may improve the visibility of defects and/or the illuminated cross-section, thus ensuring a better quality of the optical inspection.

The container and the structured light source may be configured to rotate relative to one another.

This may be particularly advantageous when the high refractive index translucent solid has an irregular surface, such as for example a rough or faceted gem, when the quality of the inspection has to be further improved or when the influence of surface defects of the solid should be completely excluded.

In an advantageous embodiment the structured light source comprises a light generator with a light structuring system comprising optical lenses configured to generate the planar light fan.

The light structuring system may comprise an oscillating laser beam which is configured to generate the planar light fan.

In advantageous embodiment the light source transport system comprises an electrical drive and control system adapted to determine and control a position of the light source along the inspection direction.

The exact position of a defect may thus be determined via the drive and control system in one coordinate and via the optical inspection zone in the other two coordinates.

In an advantageous embodiment the optical inspection device is moveably connected to the support structure.

In a further advantageous embodiment at least a part of the support structure and the light source transport system are arranged within the container and in that the structured light source is arranged within the container.

In another advantageous embodiment the structured light source may be arranged outside the container.

In an advantageous embodiment the optical inspection device comprises an aperture or collimator configured to adjust the thickness of the planar light fan, measured in a direction orthogonal to the plane defined by the planar illuminated cross-section. The thickness may be adjusted to the thickness of the high refractive index translucent solid, measured in the direction orthogonal to the plane, or to a fraction of the thickness of the high refractive index translucent solid.

Disclosed herein is a method of detecting a defect in a high refractive index solid, using an optical quality control system. The quality control system comprising, a container containing solid therein, a structured light source, an optical inspection zone configured for receiving an optical inspection device or an eye of a human observer, and a high refractive index liquid arranged in the container in a volume sufficient to fully or at least partially immerse the solid. The method comprises projecting, by means the structured light source, a planar light fan through the high refractive index solid to generate an illuminated cross-section. The illuminated cross-section is inspected for defects at the optical inspection zone, wherein the optical inspection zone is arranged for inspection along an inspection direction which is transverse to a plane (P) defined by the planar illuminated cross-section.

The method preferably comprises using an optical quality control device having a plurality of structured light sources, with each structured light source being arranged to project a planar light fan into the solid along the plane (P) at a different angle, to project the planar light fans into the solid.

The method may comprise using an optical quality control device that comprises a plurality of lenses, wherein one or more of the lenses is arranged to receive part of a planar light fan from the or each light source(s), the lenses being configured to project the received part of the planar light fan though the solid as a second planar light fan, the second planar light fan projecting along the plane (P) at a different angle to that of the received planar light fan, to project a second planar fan into the solid.

The method of detecting a defect in a high refractive index solid may comprise a step of supporting the solid in the container by means of a support means. The support means may be actuateable to displace the solid relative the structured light source(s). Alternatively, the structured light sources are actuated to move relative the solid held by the support means. The support means may comprise jaws actuateable to grip the solid. The jaws may comprise extensions configured to grip the solid such that they do not substantially interfere with the or each light fan projected into the solid.

The method may comprise inserting and/or removing the solid from the container by displacing the support means using an actuation unit. The method may comprise collect the solid from a repository of solids by using the actuation unit to displace the support means. The method may comprise cleaning the solid by a cleaning means. The actuation unit may be used to displace the support means so that the solid interface with a cleaning means operable to clean the solid prior to and/or after the step of defect detection. The method may comprise aligning the solid in the support means by means of an alignment unit, the alignment unit being operable to align the solid with respect to part of the support means. The actuation unit may be used to displace the support means so that the solid interfaces with the alignment unit.

The method of detecting a defect in a high refractive index solid may be combined with any aspect of the aforementioned optical control system in any suitable combination.

Further objects and advantageous features of the invention will be apparent from the claims, from the detailed description, and annexed drawings, in which:

DETAILED DESCRIPTION OF THE DRAWINGS

Figure 1:
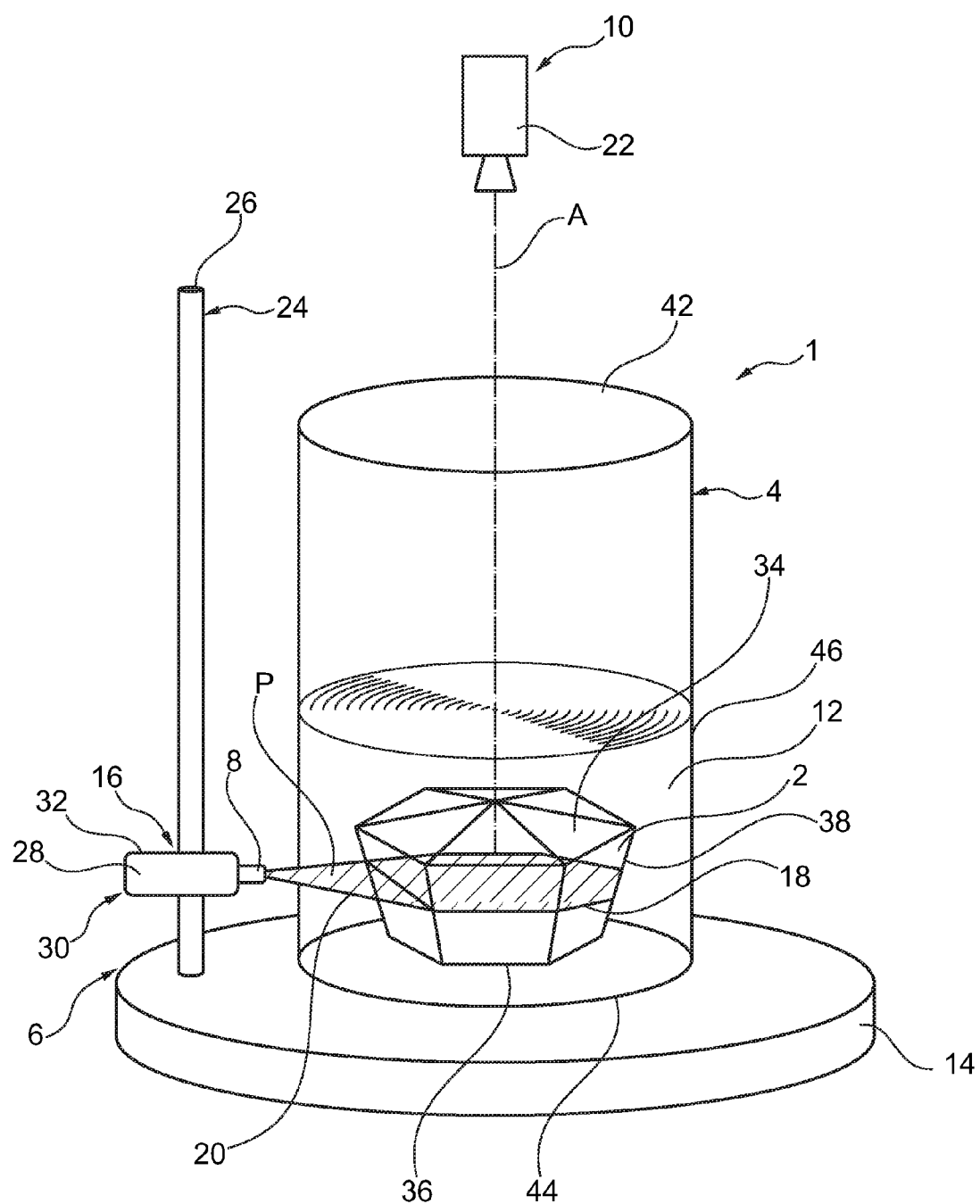
FIG. 1 is a perspective simplified schematic view of an embodiment of an optical quality control device according to the invention.
Figure 2:
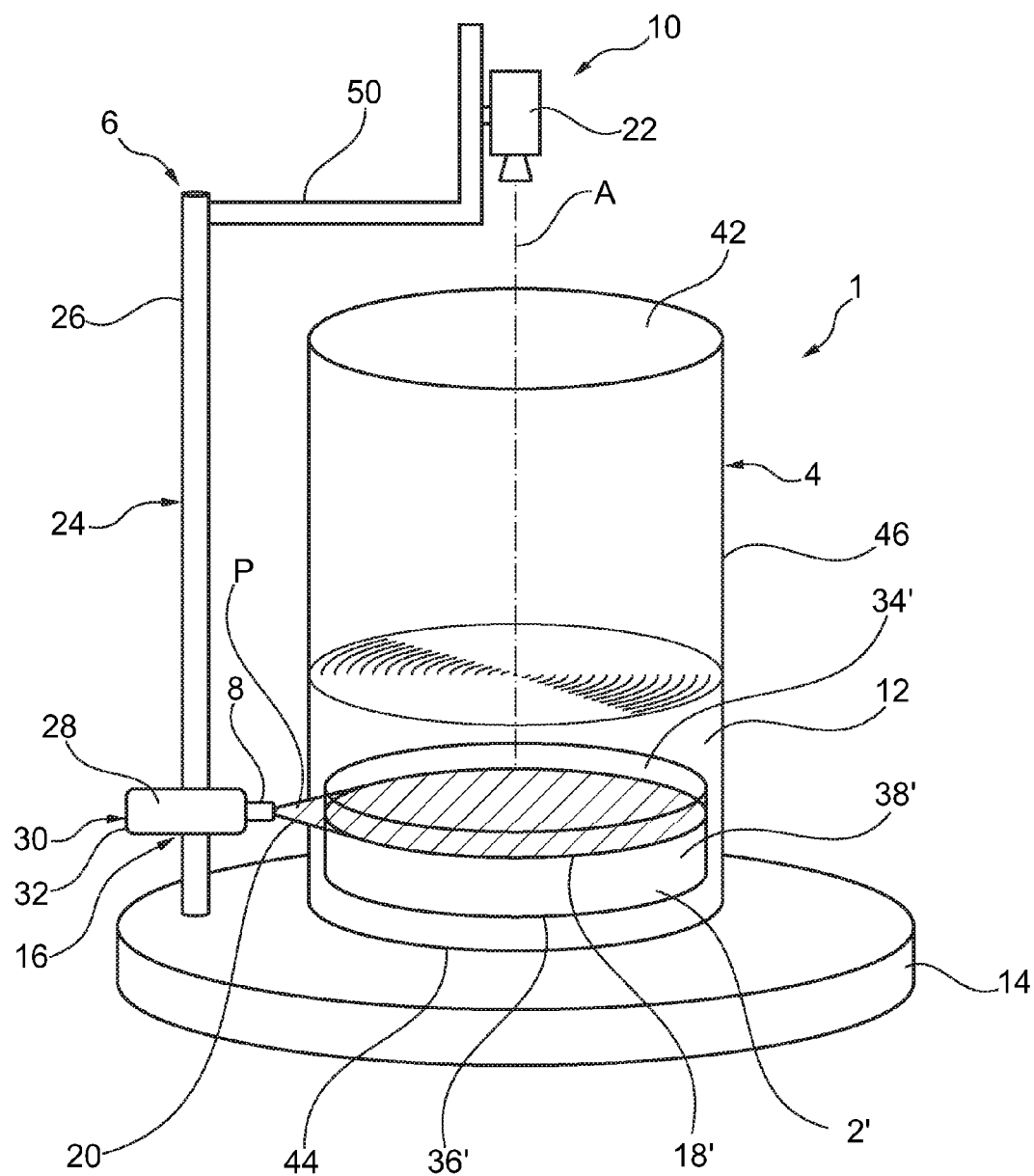
FIG. 2 is a perspective simplified schematic view of an embodiment of the invention similar to the embodiment of FIG. 1.
Figure 3:
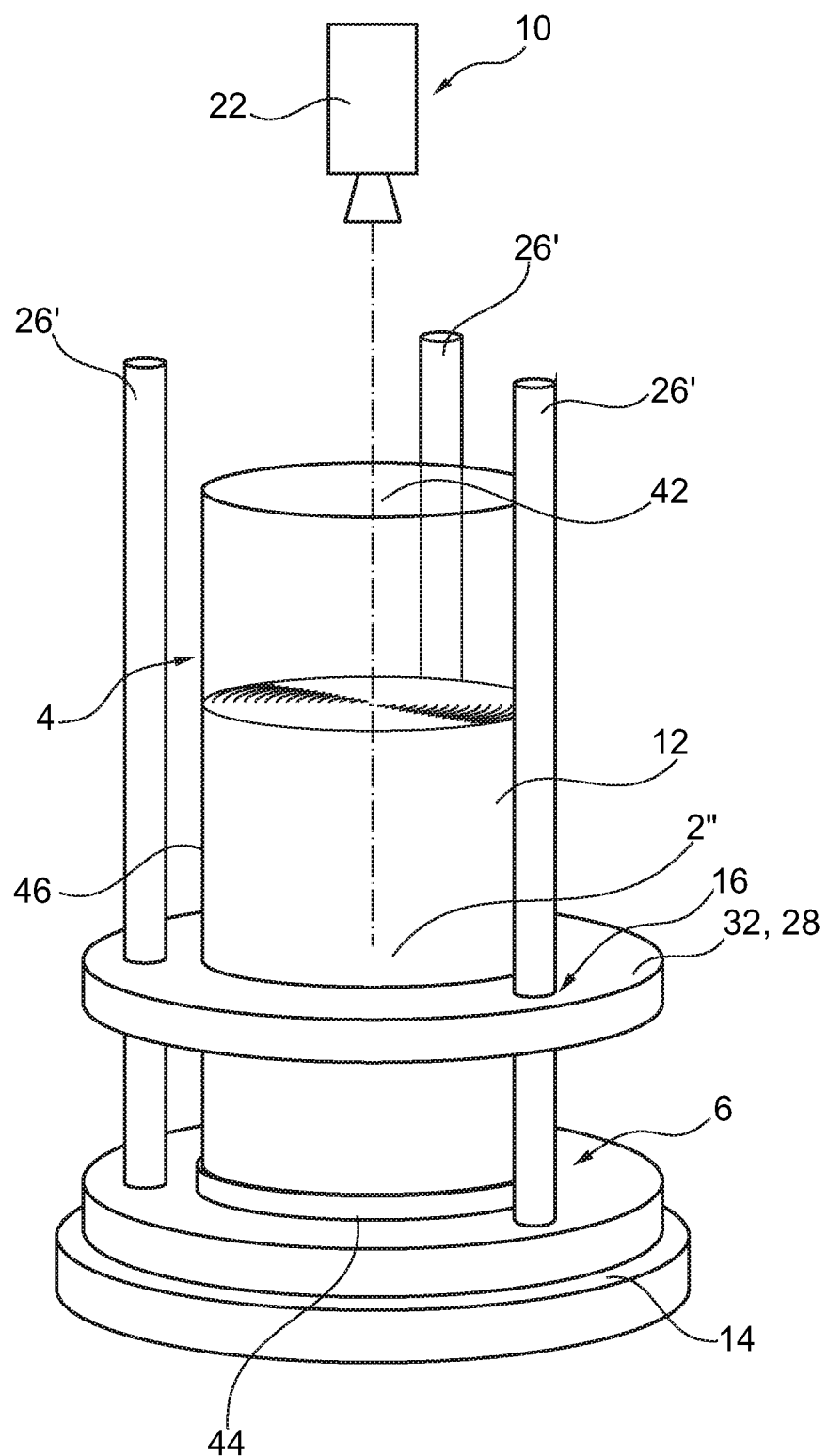
FIG. 3 is a perspective simplified schematic view of another embodiment of an optical quality control device according to the invention.
Figure 4:
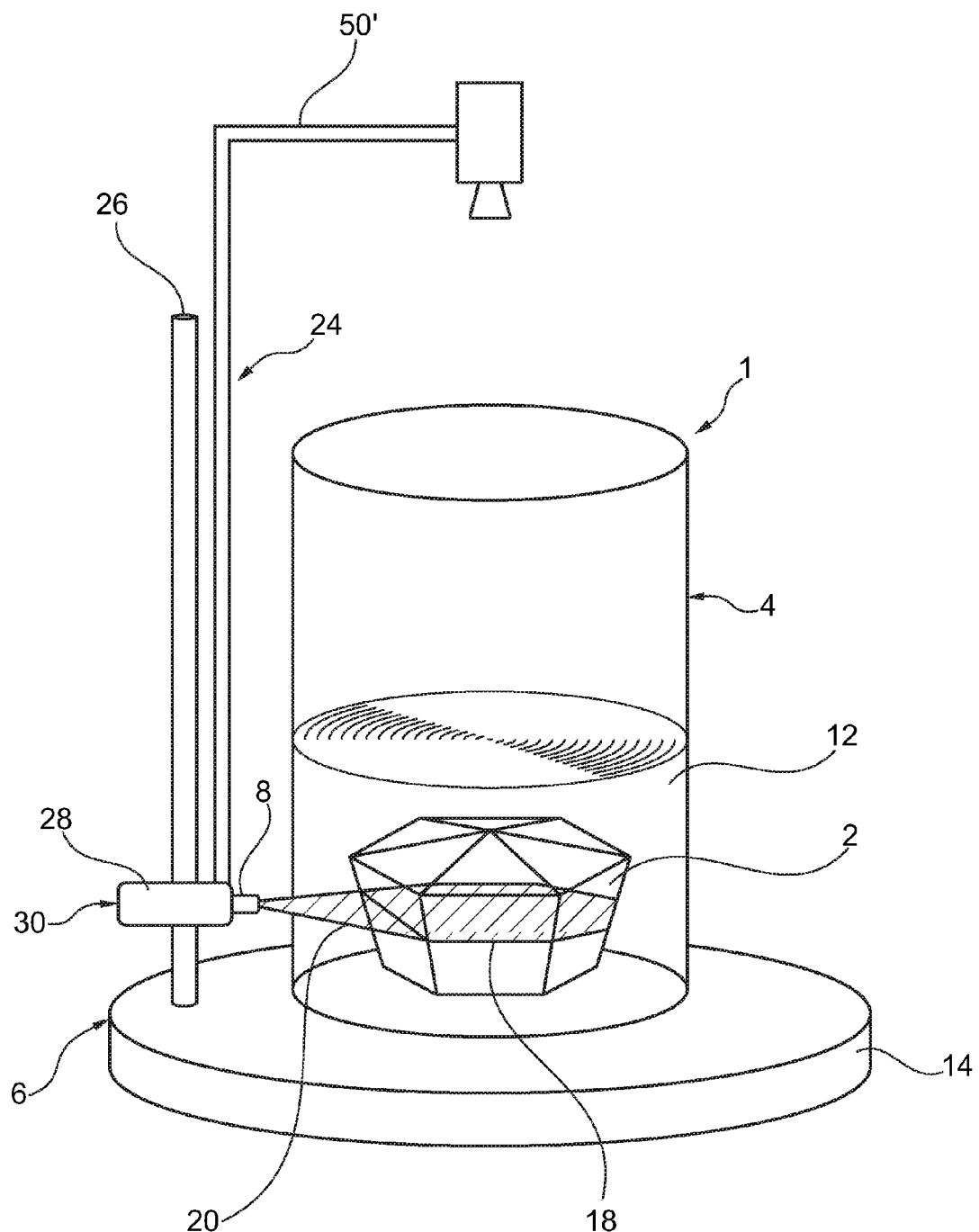
FIG. 4 is a perspective simplified schematic view of another embodiment of an optical quality control device according to the invention.

Referring to the figures, an optical quality control system 1 according to exemplary embodiments of the invention, comprises a container 4 for receiving therein a high refractive index translucent solid 2 and a volume of high refractive index liquid 12 sufficient to immerse the translucent solid completely in the liquid. A structured light source 30 is configured to project a planar light fan 20 through the high refractive index translucent solid 2, 2', 2'', 2'''. The planar light fan 20 generates an illuminated cross-section 18 in the high refractive index translucent solid 2, 2', 2'', 2'''. The illuminated cross-section 18 corresponds basically to an illuminated view of a cross-section of the high refractive index translucent solid 2, 2', 2'', 2'''. The planar light fan 20 allows raying and inspecting the high refractive index translucent solid 2, 2', 2'', 2''' without degradation. FIG. 1 shows an example of how the planar light fan 20 illuminates a cross section, by creating an illuminated cross-section 18, of a gem 2. FIGS. 2, 3 and 4 exemplify how the planar light fan 20 illuminates a cross-section, by creating an illuminated cross-section 18, of a sapphire disk 2', 2''' or a sapphire ingot 2''.

The illuminated cross-section 18 and the planar light fan 20 are configured to cover the entire cross section of the high refractive index translucent solid 2, 2', 2'', 2'''. The structured light source 30 comprises a light generator 28 including a light structuring system 8. The light structuring system 8 or the light generator 28 may be configured so that an angle of the planar light fan 20 may be adjusted to the outer shape of the high refractive index translucent solid 2, 2', 2'', 2''', for example, by adjusting the position of a lens (not shown), so that the planar light fan 20 covers the entire cross section of the solid 2, 2', 2'', 2'''.

The planar light fan 20 enters the high refractive index translucent solid 2, 2', 2'', 2''' preferably via an edge side 38, 38'. However it is possible that the planar light fan 20 enters the solid 2, 2', 2'', 2''' via the top 34, 34', for example by inverting the positions of the optical inspection device 10 or the eye of the observer and the structured light source 30. In such a configuration the light source transport system 16 may for instance be configured to displace the structured light source 30 horizontally.

An optical inspection device 10 or an eye of a human observer may be positioned in an optical inspection zone, which is arranged above the container 4 in a region close to a first end 42 of the container 4 that in the illustration represents a top end. In FIGS. 1 and 2 an inspection direction A is indicated, which is transverse to a plane P defined by the planar light fan 20, and in a particular embodiment at least approximately oriented orthogonal to a plane P defined by the planar light fan 20. The positioning of the optical inspection device 10 and the eye of an observer along the inspection direction A allows an optimal inspection of the illuminated cross-section 18.

As the illuminated cross-section 18 alone only allows the inspection of a cross section of the high refractive index solid 2, 2', 2'', 2''', the structured light source 30 may be moveably mounted on at least one inspection direction guide 26, 26' as shown in all figures. The structured light source 30 may be moved via a light transport system 16, for instance manually by the observer, so that the illuminated cross-section 18 travels through the entire high refractive index solid 2, 2', 2'', 2'''. It is possible to move the structured light source 30 from a second end 44, which in the illustration may be represented by a bottom wall 44 of the container 4, to the first end 42 of the container 4, that represents the top end in the illustrated embodiment, and thus to completely scan and inspect the high refractive index solid 2, 2', 2'', 2''' which rests with a bottom 36, 36' on the bottom wall 44 of the container 4, even if the solid 2, 2', 2'', 2''' extends from the bottom end 44 to the top end 42 of the container 4. In an advantageous embodiment the high refractive index solid 2, 2', 2'', 2''' is positioned a predetermined distance away from the bottom wall 44 of the container 4 in order to exclude or reduce the influence of the container on the inspection results. For example, the predetermined distance may be about 2-5 cm.

Instead of manually moving the structured light source 30 it is possible to have a drive and control system (not shown) installed in the light source transport system 16. The drive and control system being configured to move the light source 30 along the inspection direction guide 26, 26', from the second end 44 of the container 4 to the first end 42. The drive and control system may comprise an information interface where the observer or a computer can directly determine the actual position of the structured light source 30 in the inspection direction.

In the embodiments illustrated the inspection direction corresponds to the vertical direction, however within the scope of this invention the planar direction of the illuminated cross-section may be horizontal or in any other direction such that the inspection direction may also be in any corresponding direction transverse to planar direction of the illuminated cross-section.

The container may have an open first or top end (as illustrated) or may be closed and hermetically sealed with the refractive index liquid inside such that the container may be oriented in any direction.

If the optical inspection device 10 or the observer detects a defect the actual position of the defect can immediately be determined via its location within the illuminated cross-section and the position of the structured light source 30 in the inspection direction.

The container 4 comprising the high refractive index liquid 12 may be fully transparent as shown in the figures or alternatively it may comprise a light absorbing light receiving portion (not shown) arranged on the inner side of a side wall 46, opposite the structured light source 30. The light absorbing light receiving portion is configured to avoid reflections, which may disturb the inspection operation, from the inner side of the sidewall 46 of the container 4.

The light absorbing light receiving portion may cover the entire inner side of the container 4 with the exception of a transparent light window portion (not shown) which is configured to let the planar fan light 20 pass through for scanning the high refractive index translucent solid 2, 2', 2", 2'''. This may enhance the visibility of defects in the illuminated cross-section 18.

The structured light source 30 may comprise a laser so that the planar light fan 20 is a planar laser light fan. The light structuring system 8 may comprise a cylindrical lens which transforms the cylindrical laser beam into a plane and thus a planar laser light fan. The lens of the light structuring system 8 may be configured to be exchanged. In a preferred embodiment the laser comprises a red laser, such as a diode or ruby laser. Such a laser gives good optical penetration. However, other types of laser may also be used: a green laser is particularly advantageous when a human eye is used for inspection since the eye is more sensitive to this particular wave length than, for example, a red laser. Infrared lasers may be used for materials transparent in this spectral region when observation by eye is not important. It will be appreciated that the inspection device is configured to be sensitive to the utilised light.

Instead of using a laser it is possible to use other sources of light such as for example strong LED lights which emit a planar light fan as described. Other light sources and combinations thereof may also be possible and fall within the scope of this invention.

Instead of comprising a cylindrical lens, the light structuring system may comprise other optics or a system that allows oscillating the laser beam so that it generates the planar laser light fan 20. Instead of letting the laser beam oscillate it is possible to let the laser beam rotate thus creating a planar laser plane which is configured to be projected through the high refractive index solid 2, 2', 2", 2'''. If a rotational motion of the laser beam is used, the structured light source 30 may be shielded so that the laser beam only projects towards the container 4 and the solid 2, 2', 2", 2''', respectively.

The optical quality inspection system 1 may further comprise a support structure 6 with a base 14 and a frame 24 as shown in the FIGS. 1 to 3. The base 14 is configured to hold and position the container 4. It is possible that the base 14 comprises a recess (not visible) to embed the container 4. Moreover the container 4 may be fixedly connected to the base 14. The frame 24 comprising the inspection direction guide 26, 26' may be fixedly connected to the base 14, for example via a screw-thread connection.

In FIG. 1 the optical inspection device 10 is shown arranged separately from the support structure 6. FIG. 2 shows the optical inspection device 10 connected to the support structure 6 via a connecting portion 50, of the frame 24. The optical inspection device 10 may be moveably fixed to the connecting portion 50, so that the position can be adjusted along the inspection direction A.

In an advantageous embodiment illustrated in FIG. 4, the optical inspection device 10 may be connected via the connecting portion 50' to the structured light source 30 or the light source transport system 16 so that the light source 30 always moves together with the optical inspection device 10, thus keeping the distance between the top 34 of the high refractive index translucent solid 2, 2', 2", 2''' at a constant level. In order to initially adjust the distance between the optical inspection device 10 and the high refractive translucent solid 2, 2', 2", 2''' it may be possible to move and releasably fasten the optical inspection device 10 in a direction orthogonal to the plane P on the connecting portion 50'. It is possible that the base 14 is configured so that the container 4 may rotate relative to the structured light source 30. This can be achieved for example by a drive configured to rotate a plate or the like, which is installed on the base 14 and configured to support the container 4. Thus the plate may be installed in between the base 14 and the bottom wall 44 of the container 4. It is also possible to move the structured light source 30 for instance by moving the frame 24, so that the structured light source 30 moves relative to the container 4. Such a rotation allows inspecting the high refractive index translucent solid 2, 2', 2", 2''' from all angles around the side 38, 38' of the solid 2, 2', 2", 2'''. Surface defects or irregularities on the high refractive index translucent solid 2, 2', 2", 2''' may thus be easily spotted and eliminated during the inspection.

The optical inspection device 10 may comprise a camera 22 which is electronically connected to a computer (not shown) configured to analyse the images of the illuminated cross-section 18 taken by the camera 22. Such an optical inspection system 1 comprising an analysing computer may be installed in a production line for example for sapphire disks 2', 2''' or sapphire ingots 2", in which the computer is configured to activate a system that sorts out sapphire disks 2', 2''' or sapphire ingots 2" with a defect.

The structured light source 30 and the light source transport system 16 may be embedded in a moveable element 32 as shown in FIG. 3. The moveable element 32 is in the shape of a flattened ring and configured to embed the components of the structured light source 30 and the light source transport system 16. The moveable element 32 may comprise one or of a plurality of light generators 28 so that a plurality of planar light fans 20 may project towards the solid 2" from different angles. In FIG. 3 three inspection direction guides 26' are shown, configured to guide the movement of the moveable element 32 in the inspection direction which in the illustrated embodiment is the vertical direction. The moveable element 32 is configured to move from the second end 44 to the first end 42 of the container 4. The inspection direction guides 26' are fixedly connected to the base 14. This particular example is preferred for defect detection in thick solids, one such example is a sapphire ingot.

Figure 5:
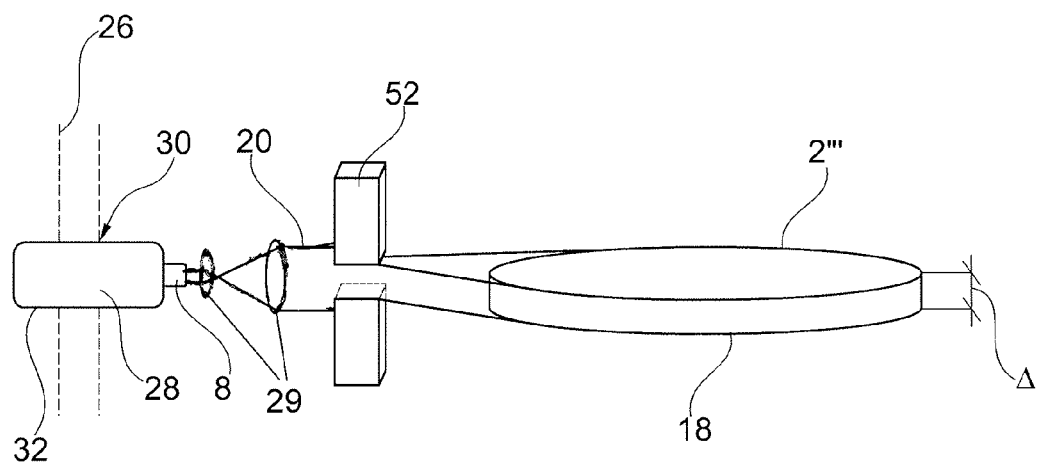
FIG. 5 is a perspective simplified schematic view of a part of an embodiment of an optical quality control device comprising an aperture or collimator illustrated without container and without high refractive index liquid.

FIG. 5 illustrates a schematic view of the structured light source 30, an aperture 52 or collimator and a high refractive index translucent solid 2". The aperture 52 may be configured to be adjustable, so that the thickness of the planar light fan 20 measured in the direction orthogonal to the plane P defined by the planar light fan 20 can be changed. The thickness D of the high refractive index translucent solid 2''' is also measured in a direction orthogonal to the plane P. The embodiment of FIG. 5 is just schematic, shown without the container 4 and without the high refractive index liquid 12. The aperture 52 may be arranged within the container 4 or outside of the container 4. Optical lenses 29 may be arranged between the light source and the aperture, in order to spread or focus the light emitted from the light source for optimal light intensity, direction and homogeneity before being structured by the aperture 52.

The structured light source 30 may, in an embodiment, be configured to illuminate the whole high refractive index translucent solid 2''' at once. This embodiment may be useful especially for relatively thin translucent solids. The thickness of the planar light fan 20 may be adapted via the aperture 52 to the thickness D of the high refractive index translucent solid 2, 2', 2", 2'''. This allows to further speed up the inspection process.

The container 4 shown in the figures has a cylindrical shape and is transparent. However other shapes such as for example cubical, cone shaped, or irregular shapes fall within the scope of the invention. In embodiments where the structured light source 30 is external the container, the container may advantageously have a shape which is planar in the region that the light fan 20 propagates through. In this way the distortive effect of the container wall is minimised.

Figure 6:
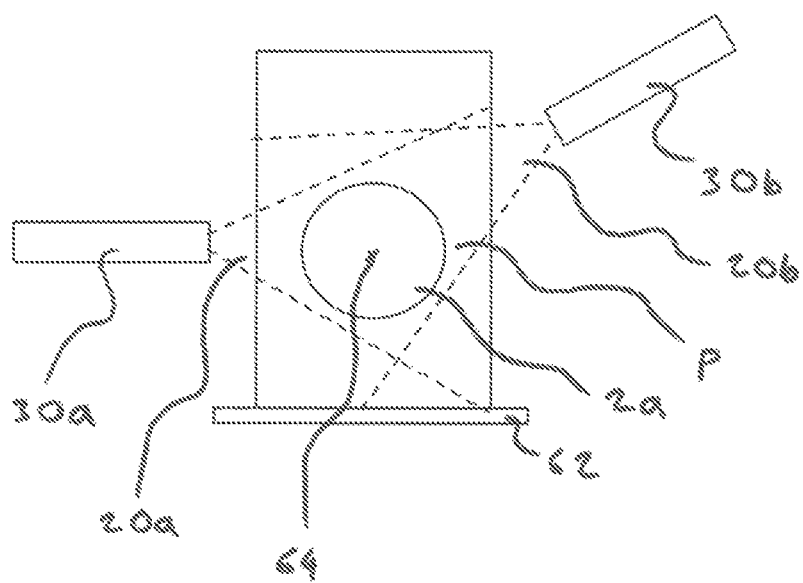
FIG. 6 is a perspective cross-sectional view of an embodiment of an optical quality control device according to the invention.

FIG. 6 shows a further embodiment of an optical quality control system. In this embodiment the optical quality control system is configured to detect defects with a disc shaped solid 2a that is arranged with the plane of the disc in a vertical plane. An example of such a disc is sapphire watch glass, which is generally about 24 mm-40 mm in diameter and about 2-6 mm thick. Although the embodiment is illustrated with a disc shaped solid it will be appreciated that the embodiment is suitable for use with other shaped solids. Moreover, it will be appreciated that the optical quality control system may be configured to detect defects with the solid arranged in other planes. The solid 2a is arranged in a container 60 which is rectangular in cross-section, however it will be appreciated that other shaped containers may be used. The container 60 is secured by mounting means 62, which in this example is a base in abutment with a lower edge of the container. The mounting means may alternatively or additionally comprise a clamp which abuts the sides of the container.

There are two structured light sources 30a and 30b, however it will be appreciated that there may be one or more structured light source. The structured light sources 30a and 30b are arrange to project corresponding planar light fans 20a and 20b into the solid from different angles, whilst all being coincident along the plane (P) of the illuminated cross-section. It is preferred that each of the structured light sources is arranged such that their light fan covers the whole cross-section of the solid, as shown in FIG. 6. Such an arrangement is achieved by disposing the structured light sources a suitable distance away from the solid, such that the projected planar light fan encompasses the cross-section of the solid. For example, the structured light sources may be disposed about a central axis 64 of the solid 2. In this example the structured light sources are disposed at an angular increment of 135° to each other about the central axis 64 and are arranged to project the centre line of the planar light fan in approximate alignment with the axis 64. It will be appreciated that various arrangements of the structured light sources are possible. It is also preferred that the coincident planes of the light fans are in the same plane as that of the disc shaped solid 2a.

Figure 7:
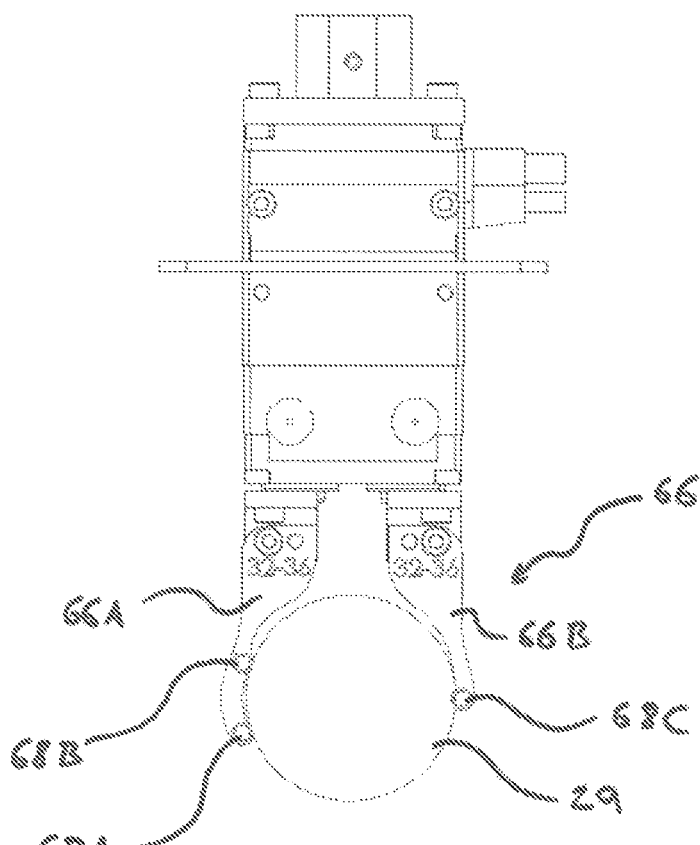
FIG. 7 is a perspective view of a support means of the device of FIG. 6.

The solid 2a is held in the container by support means 66, as best seen in FIG. 7. In this embodiment the support means comprises opposed jaws 66A, 66B which are operable to move between an open un-clamped position and a closed clamped position (as shown in FIG. 7) wherein the solid is supported. In an advantageous embodiment the jaws 66A 66B each comprise one or more protrusions 68. In the example shown the jaw 66A has two protrusions 68A, 68B and the jaw 66B has a single protrusion 68C. The protrusions are conveniently arranged to support the solid 2a, in this example by a three point support. Conveniently, the protrusions are also arranged and configured such that they do not substantially interfere with the light fans. In this way the support means 66 can be used to transfer the solid to and from the container and support the solid during defect detection.

Although in the above example the support means 66 comprises jaws, other configurations may be used. For example, the support means 66 may comprise an arm with several adhesive points that adhere to the solid 2a.

To enable scanning of the full thickness of the solid 2a (wherein the thickness is defined as the direction parallel to the central axis 64), the device is configured such that the structured light sources can move relative the solid in the thickness direction. In general it is preferred that the thickness direction is aligned to that of the inspection direction. It will be appreciated that such movement can either be achieved by movably mounting the structured light sources, for example on actuators, or by movably mounting the solid 2a. In the example embodiment the structured light sources are held in a fixed position and the solid is displaced by an actuated support means 66, which is operable to move the solid in the thickness direction. Examples of other arrangements are shown in FIG. 10, which is discussed in more detail in the following.

In all of the embodiments it is advantageous that the light fans have a thickness of about 0.05-1 mm. In this way the precise location of defects in the thickness direction can be determined.

Figure 8:
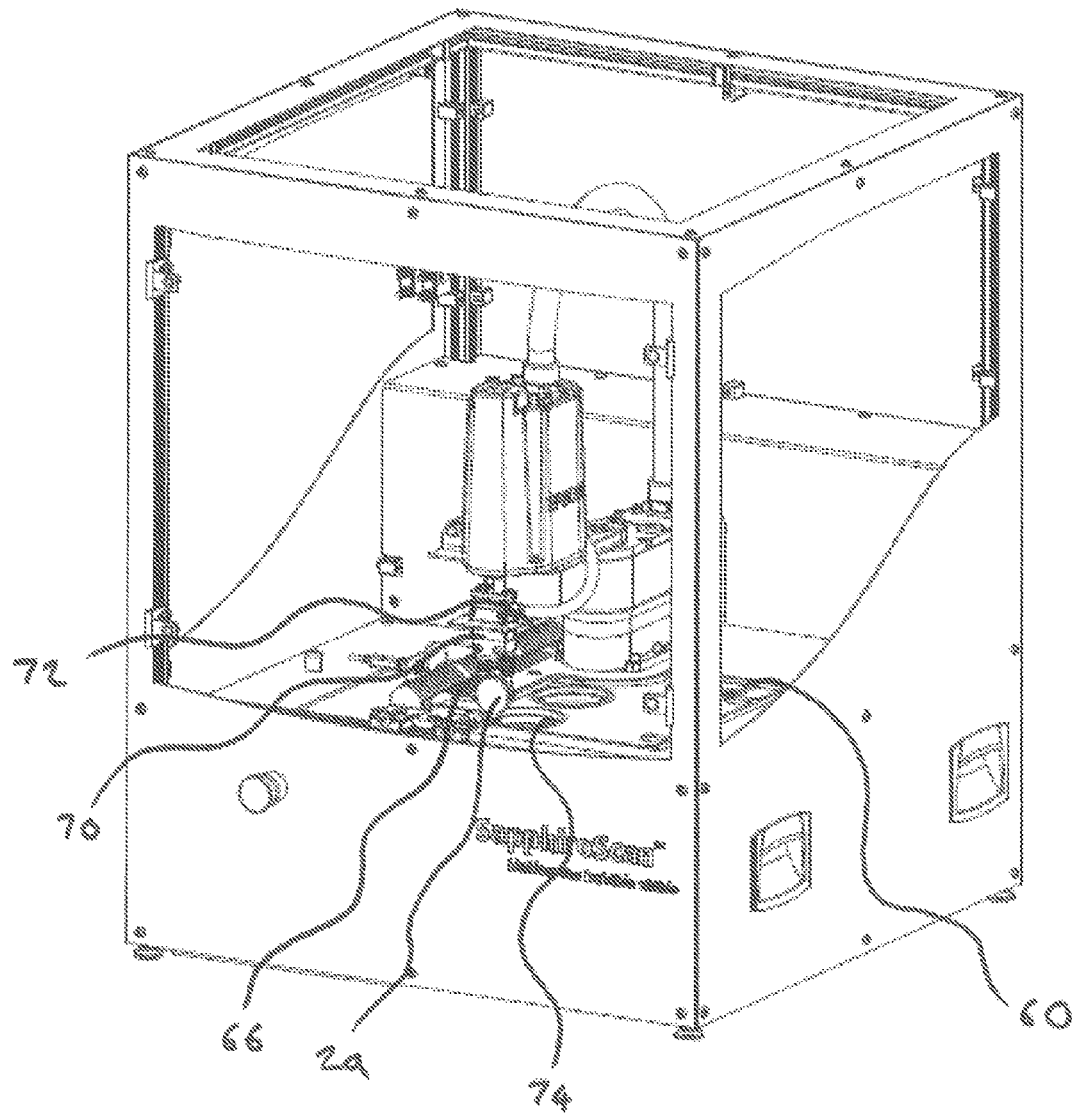
FIG. 8 is a perspective view of an actuation unit and repository of the device of FIG. 6.

FIG. 8 shows further components which may conveniently be included in the optical quality control system. In this embodiment the support means 66 is connected to an actuation unit 70 which is operable to actuate the support means in various directions. In a preferred embodiment the actuation unit comprises an automated arm, however it may also be manually operated. Conveniently, the actuation unit 70 can be used to displace the support means 66 to thereby displace the solid 2a relative the structured light sources in the thickness direction as discussed above. The actuation unit may also be operable to insert and remove the solid from the container 60. In an advantageous embodiment the actuation unit is configured to accurately position the solid in an inserted position, wherein the plane of the disc shaped solid, or other suitable reference plane, is aligned to the plane of the or each light fan(s) such that the solid is aligned for scanning.

The actuation unit 70 may further be operable to position the support means 66 for collecting a solid 2a to be tested from a repository 72. Prior to being tested the solid 2a may be cleaned by a cleaning means 74 such that it is suitable for testing. An example of suitable cleaning means is a bath comprising a medium, such as distilled water, and ultrasonic excitation means operable to transfer ultrasonic waves to the solid. Alternatively, the cleaning means may comprise a chemical cleaning system, such as a bath containing a solvent. The actuation unit 70 may be configured to move the solid 2a to the cleaning means 74 from the repository 72. The actuation unit 70 may be further configured to move the solid 2a to the container 60 from the cleaning means 74. The actuation unit 74 may further be configured to move the tested solid from the container 60 and, based on the quality of the solid, store the solid in a pass or fail position, which may be within the repository 72 of a further repository. The actuation unit 70 may be further configured to move the tested solid 2a from the container 60 to the cleaning means 74 prior to storage.

Figure 9:
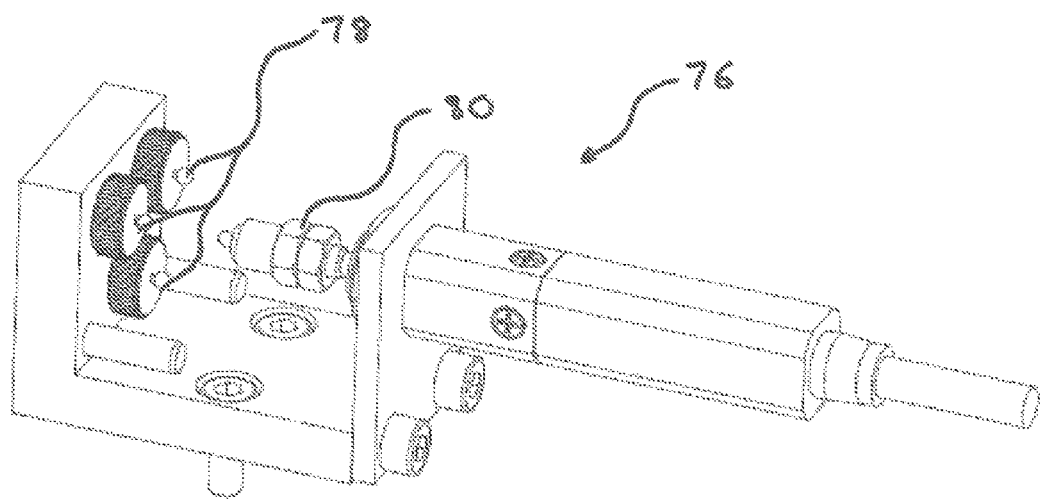
FIG. 9 is a perspective view of an alignment means of the device of FIG. 6.

In an advantageous embodiment, between transfer of the solid from the repository 72 to the container 60, the solid 2a may be aligned for scanning using an alignment unit 76. A suitable alignment unit 76 is shown in FIG. 9 and comprises abutment members 78 for abutting a first side of the solid. In a preferred example the abutment members comprise a three point support. An actuator 80 is operable to engage with an opposed second side of the solid such that the solid is pressed into contact with the abutment members and thereby displaced into alignment in the support means 66. When the solid is a sapphire, it is preferred that a tip of the support members 78 and actuator 80 comprises a ruby so as not to mark the sapphire. Other suitable alignment means may comprise an aligned slot, which the solid and support means 66 are inserted into. The alignment unit 78 ensures that the solid is correctly aligned in the support means 66 for testing.

In the above embodiment one or more of the actuation unit 72, support means 66, structured light source(s) and inspection device are controlled by a control unit, such as a PC. In this way the optical quality control system is conveniently partially or fully automated.

FIGS. 10A-E show various embodiments of an optical quality control system which is similar to the embodiment of FIG. 3. It is preferred that these embodiments are used to test for defects in thick solids, such as those in the order of about 4-60 cm. For example a sapphire ingot can be scanned to prior to being cut into discs for use in watch faces or semi-conductors. However, it will be appreciated that their arrangement can be used for other shaped solids.

Figures 10A, 10B:
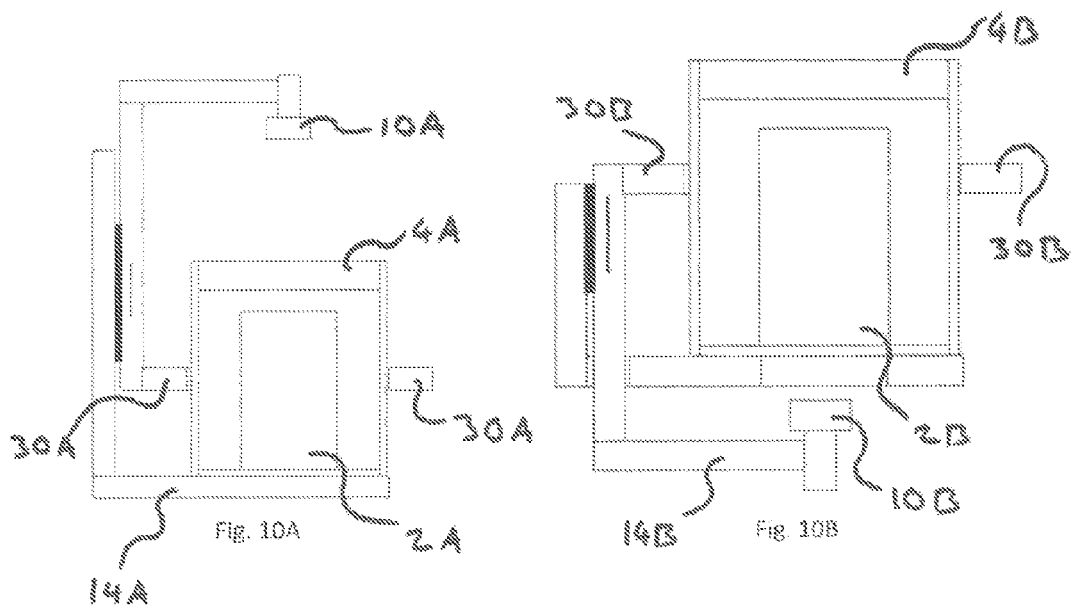
FIG. 10 is a side cross-sectional schematic view of various embodiments of the invention which are similar to the embodiment of FIG. 3.

Referring now to FIG. 10A, the solid 2A is arranged in the container 4A both of which remain in a fixed position relative a base 14A. The structured light sources 30A move to enable the entire thickness of the solid 2A to be measured. The optical inspection device 10A is arranged to move with the structured light sources 30A. A suitable structure for mounting the structured light sources and inspection device 10A to is provided in the embodiment of FIG. 3.

Referring now to FIG. 10B, the solid 2B is arranged in the container 4B both of which remain in a fixed position relative a base 14B. As in the embodiment of FIG. 10A, the structured light sources 30B and inspection device 10B move to enable the entire thickness of the solid 2B to be measured. However, the optical inspection device 10B is arranged to view the illuminated cross-section via an aperture thought the base 14B.

Figures 10C, 10D:
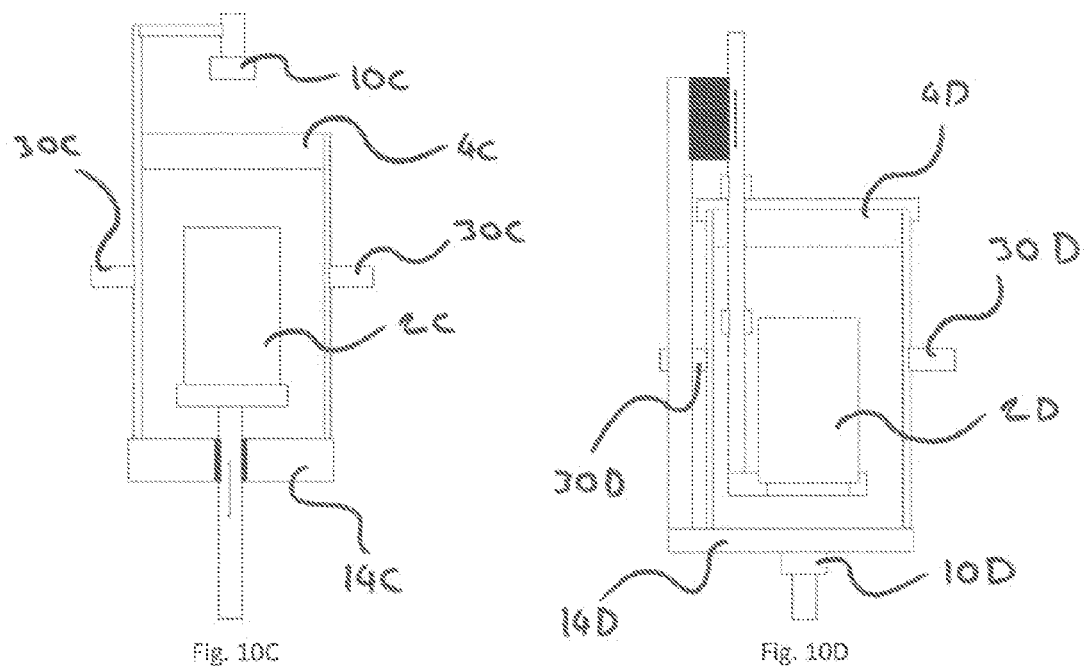
Figure 10E:
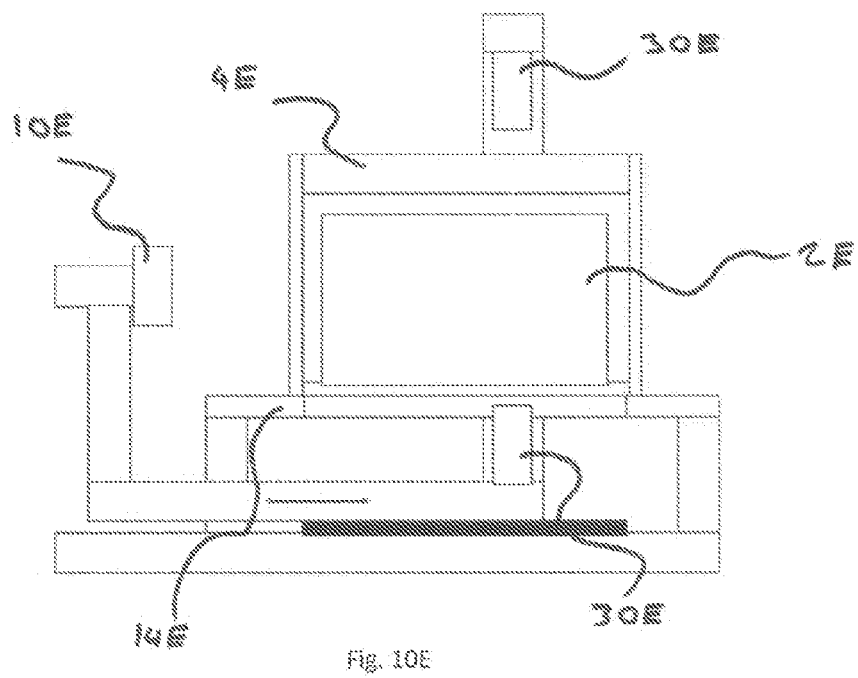

Referring now to FIG. 10C, the solid 2C is arranged in the container 4C, however the solid 2C is moved relative the container via an actuator that extends through an aperture in the base 14C and bottom of the container. In this example the container 4C, structured light sources 30C and inspection device 10C remain in a fixed position relative a base 14A. In FIG. 10D the arrangement is similar to that of FIG. 10C, however the actuator extends into the container 4D via the upper open end of the container. Referring now to FIG. 10E, the arrangement is similar to that of FIG. 10A, however the structured light sources 30E and inspection device 10E move in a horizontal plane.

Figure 11A:
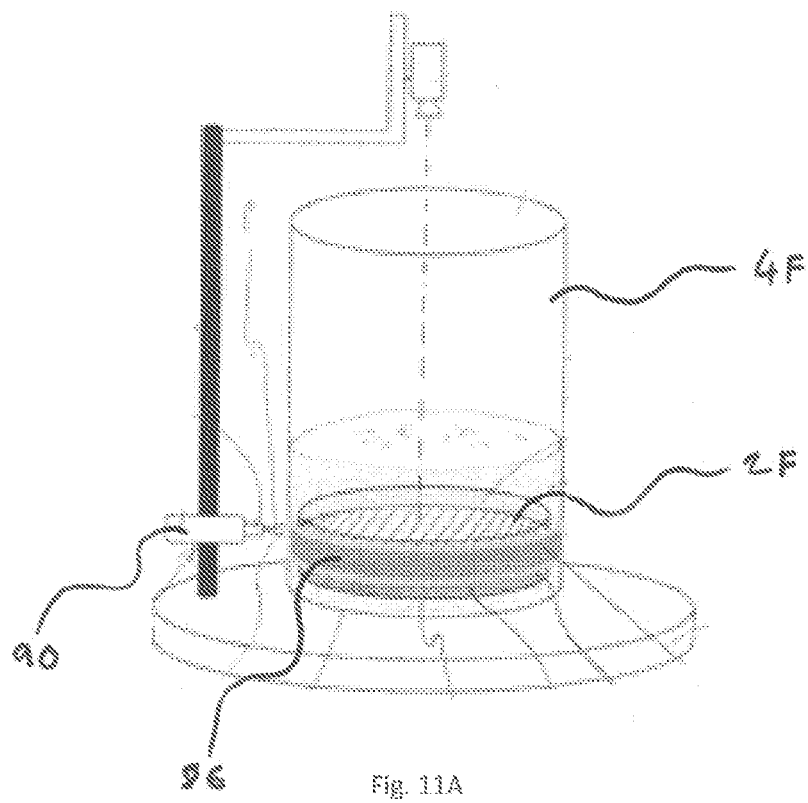
FIG. 11 is a perspective schematic view of an embodiment wherein the structured light source comprises a plurality of micro-lenses.
Figure 11B:
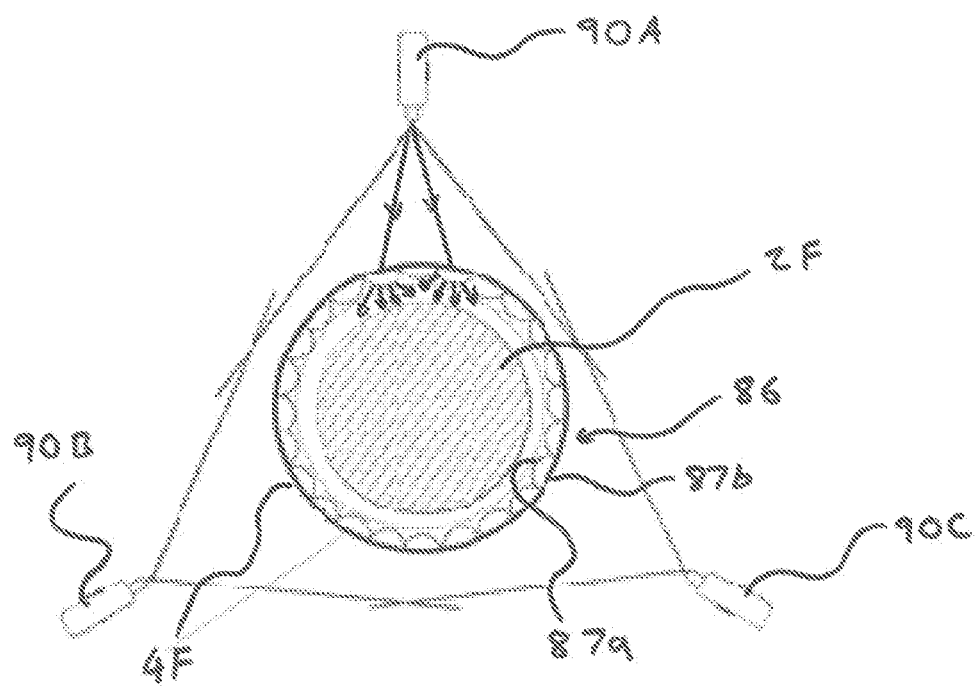

In an embodiment, the structure light source may comprise a plurality of lenses 86, such as array of cylindrical lenses, array of microlenses or a lenticular film, which may be arranged around the solid 2F, as shown in FIGS. 11A and 11B. The lenses 86 are configured such that light from the light source 90 passes though lenses and is subsequently projected through the solid 2F. As shown in the illustrated embodiment, the light may be part of the planar light fan 88. The lenses are further configured to generate, from the part of the light fan passing there through, secondary light fans 92A-92B (in the example figure only two secondary light fans are shown for clarity). The secondary light fans project along the same plane (P) as the planar light fan 88, however they extend in different directions and illuminate the high refractive index solid at different angles. Advantageously, the lenses increase the number of directions that the light extends thought the illuminated cross-section such that defects are more likely to be identified.

Although in the above embodiment the light fan 88 is subject to approximately 7 lenses 86, it will be appreciated that other numbers of lenses are possible. It will also be appreciated that the lenses may be used with a single structured light source 90 (as shown in FIG. 11A) or a plurality of structured light sources 90A-B, such as three (as shown in FIG. 11B).

A suitable example of a lens 86 comprises a curved receiving surface 87a for receiving the planar light fan 88, and a convex projecting surface 87b for projecting the second light fan 92.

In the example the lenses are arranged such that they extend along the thickness of the solid. However, the lenses may alternatively comprise a thin strip which moves with the structured light sources whilst the structured light sources move relative the solid, for example they may be included on the movable element 32 of the embodiment of FIG. 3.

A suitable thickness for the lenses 86 is 1-5 mm in the direction of the optical axis, in the case when the lenses are moving with the light source. A suitable diameter of lens is 0.5-5 mm. In an advantageous embodiment the lenses 86 are shaped in the form of curved ridges, for example semi-cylindrical, aligned perpendicular to the plane P. A suitable lenses is the Lenticular material by Lenstarlenticular (Lenstatlenticulat.com).

In the example embodiment the lenses 86 are fixed to the container 4F, for example by an adhesive. The lenses may be attached to an inside of the container as shown, or the outside. In a variant, the lenses may also be mounted on a support surrounding the container, relatively movable to the container.

In the aforementioned embodiments the system has been described when used in conjunction with a translucent solid. Translucent in this context could refer to an unpolished solid. It is to be noted that the translucent appearance occurs due to the pre-polished rough surface, which causes light scattering. The effect of the rough surface is negated by the system due to the matching of the refracting index of the liquid and solid. It is desirable to measure the quality of the solid before polishing because if the quality of the solid is found to be unsatisfactory, then polishing is obviated. However, it will be appreciated that the system can be used on transparent solids. For example, after a solid has been polished it may be inspected for validation or as a second step in the manufacturing process to precisely locate a defect so that it can be removed or the usable parts of the solid cut-out. Accordingly, the system can be used to measure any light permeable solid.

The optical quality control inspection system 1 according to the invention has many possible applications. It may be used in the quality control of ingots of crystalline materials, technical crystals, as well as manufacturing of sapphire glasses for watch covers, sapphire substrates for semiconductor applications, displays for mobile phones, TVs, and computers or lenses for video- and photo cameras.

The invention claimed is:

1. An optical quality control system for detecting a defect in a light permeable high refractive index solid, with a refractive index greater than 1.6, the quality control system comprising:
a container configured to receive the solid therein;
a structured light source;
an optical inspection zone for receiving an optical inspection device or for allowing a human observer to inspect by eye said high refractive index solid received in the container; and
a high refractive index medium with a refractive index greater than 1.6 for insertion in the container in a volume sufficient to fully or at least partially immerse the high refractive index solid,
wherein the structured light source is configured to project a planar light fan through the high refractive index solid to generate an illuminated cross-section in the high refractive index solid and wherein the optical inspection zone is arranged for inspection of an immersed portion of the illuminated cross-section in an inspection direction transverse to a plane (P) defined by the planar illuminated cross-section, and wherein at least a part of the support structure and the light source transport system are arranged within the container and in that the structured light source is arranged within the container.

2. The optical quality control system according to claim 1, comprising a light source transport system configured to enable the light source to be displaced along the container.

3. The optical quality control system according to claim 1, wherein the optical inspection zone is adapted for inspection of the illuminated cross-section in said inspection direction (A) essentially orthogonal to the plane (P).

4. The optical quality control system according to claim 1, wherein the structured light source comprises a laser generating the planar light fan.

5. The optical quality control system according to claim 2, wherein the light source transport system is configured to transport the structured light source along the inspection direction from a second end of the container to said first end so that the whole high refractive index solid can be scanned by the planar light fan.

6. The optical quality control system according to claim 1, wherein the container comprises a light absorbing surface portion arranged opposite the light source configured to reduce reflection of light within the container.

7. The optical quality control system according to claim 1, wherein the container and the structured light source are configured to rotate relative to one another.

8. The optical quality control system according to claim 1, wherein the structured light source comprises a light generator with a light structuring system comprising optical lenses configured to generate the planar light fan.

9. The optical quality control system according to claim 8, wherein the light structuring system comprises an oscillating laser beam which is configured to generate the planar light fan.

10. An optical quality control system according to claim 5, wherein the light source transport system comprises an electrical drive and control system adapted to determine and control a position of the light source in the inspection direction.

11. The optical quality control system according to claim 1, wherein the structured light source is arranged outside the container.

12. The optical quality control system according to claim 1, comprising an aperture or collimator configured to adjust the thickness of the planar light fan (20), measured in a direction orthogonal to the plane (P) defined by the planar illuminated cross-section.

13. The optical quality control system according to claim 1 comprising a support structure, wherein the optical inspection device is moveably connected to the support structure.

14. The optical quality control system according to claim 2, comprising a connecting portion configured to connect the optical inspection device to the structured light source or the light source transport system so that the optical inspection device may be displaced in the inspection direction by the light source transport system together with the structured light source.

15. The optical quality control system according to claim 1, wherein the planar light fan comprises a plurality of light beams which diverge when viewed in the inspection directions and which are aligned in the plane (P).

16. The optical quality control system according to claim 1, wherein the illuminated cross-section extends at least over the whole cross-section of the high refractive index solid.

17. An optical quality control system for detecting a defect in a light permeable high refractive index solid with a refractive index greater than 1.6, the quality control system comprising:
a plurality of structured light sources, with each structured light source being arranged to project a planar light fan into the solid along the plane (P) at a different angle to generate an illuminated cross-section in the high refractive index solid; an optical inspection zone for receiving an optical inspection device or for allowing a human observer to inspect by eye said high refractive index solid received in the container; and
a high refractive index medium with a refractive index greater than 1.6 for insertion in the container in a volume sufficient to fully or at least partially immerse the high refractive index solid,
wherein the optical inspection zone is arranged for inspection of an immersed portion of the illuminated cross-section in an inspection direction transverse to a plane (P) defined by the planar illuminated cross-section.

18. The optical quality control system according to claim 17, wherein the plurality of structured light sources are disposed about a central axis of the high refractive index solid which is aligned to the inspection direction.

19. An optical quality control system for detecting a defect in a light permeable high refractive index solid with a refractive index greater than 1.6, the quality control system comprising:
a container configured to receive the solid therein;
a structured light source;
an optical inspection zone for receiving an optical inspection device or for allowing a human observer to inspect by eye said high refractive index solid received in the container; and
a high refractive index medium with a refractive index greater than 1.6 for insertion in the container in a volume sufficient to fully or at least partially immerse the high refractive index solid,
wherein the structured light source is configured to project a planar light fan through the high refractive index solid to generate an illuminated cross-section in the high refractive index solid and wherein the optical inspection zone is arranged for inspection of an immersed portion of the illuminated cross-section in an inspection direction transverse to a plane (P) defined by the planar illuminated cross-section, wherein the structured light source comprises a plurality of lenses, wherein one or more of the lenses is arranged to receive part of a planar light fan from the one or more light source(s), the lenses being configured to project the received part of the planar light fan through the solid as a secondary planar light fan, the secondary planar light fan projecting along the plane (P) at a different angle to that of the received part of the planar light fan.

20. The optical quality control system according to claim 19, wherein the lenses are connected to a periphery of the high refractive index solid or the container.

21. A method of detecting a defect in a high refractive index solid with a refractive index greater than 1.6, using an optical quality control system, the quality control system comprising:
a container containing solid therein;
a structured light source;
an optical inspection zone configured for receiving an optical inspection device or for allowing a human observer to inspect by eye the high refractive index solid; and
a high refractive index medium with a refractive index greater than 1.6 arranged in the container in a volume sufficient to fully or at least partially immerse the high refractive index solid,
the method comprising:
projecting, from the structured light source, a planar light fan through the high refractive index solid to generate an illuminated cross-section,
inspecting the illuminated cross-section for defects at the optical inspection zone,
wherein the optical inspection zone and solid are arranged for inspection of an immersed portion of the solid along an inspection direction which is transverse to a plane (P) defined by the planar illuminated cross-section, wherein the optical quality control device comprises a plurality of structured light sources, with each structured light source being arranged to project a planar light fan into the solid along the plane (P) at a different angle; and
the method comprising a step of projecting the planar light fans into the high refractive index solid.

22. A method of detecting a defect in a high refractive index solid with a refractive index greater than 1.6, using an optical quality control system, the quality control system comprising:
a container containing solid therein;
a structured light source;
an optical inspection zone configured for receiving an optical inspection device or for allowing a human observer to inspect by eye the high refractive index solid; and
a high refractive index medium with a refractive index greater than 1.6 arranged in the container in a volume sufficient to fully or at least partially immerse the high refractive index solid;
the method comprising projecting, from the structured light source, a planar light fan through the high refractive index solid to generate an illuminated cross-section, inspecting the illuminated cross-section for defects at the optical inspection zone, wherein the optical inspection zone and solid are arranged for inspection of an immersed portion of the solid along an inspection direction which is transverse to a plane (P) defined by the planar illuminated cross-section, wherein the optical quality control device comprises a plurality of lenses, wherein one or more of the lenses is arranged to receive part of a planar light fan from the or each light source(s), the lenses being configured to project the received part of the planar light fan through the high refractive index solid as a secondary planar light fan, the secondary planar light fan projecting along the plane (P) at a different angle to that of the received planar light fan,
and the method comprising using the or each lens to project a second planar fan into the high refractive index solid.

23. The optical quality control system according to claim 17, comprising a light source transport system configured to enable the light source to be displaced along the container.

24. The optical quality control system according to claim 23, wherein the light source transport system is configured to transport the structured light source along the inspection direction from a second end of the container to said first end so that the whole high refractive index solid can be scanned by the planar light fan.

25. An optical quality control system according to claim 23, wherein the light source transport system comprises an electrical drive and control system adapted to determine and control a position of the light source in the inspection direction.

26. The optical quality control system according to claim 17, wherein the optical inspection zone is adapted for inspection of the illuminated cross-section in said inspection direction (A) essentially orthogonal to the plane (P).

27. The optical quality control system according to claim 17, wherein the container comprises a light absorbing surface portion arranged opposite the light source configured to reduce reflection of light within the container.

28. The optical quality control system according to claim 17, comprising an aperture or collimator configured to adjust the thickness of the planar light fan, measured in a direction orthogonal to the plane (P) defined by the planar illuminated cross-section.

29. The optical quality control system according to claim 17 comprising a support structure, wherein the optical inspection device is moveably connected to the support structure.

30. The optical quality control system according to claim 17, wherein the illuminated cross-section extends at least over the whole cross-section of the high refractive index solid.

31. The optical quality control system according to claim 19, comprising a light source transport system configured to enable the light source to be displaced along the container.

32. The optical quality control system according to claim 31, wherein the light source transport system is configured to transport the structured light source along the inspection direction from a second end of the container to said first end so that the whole high refractive index solid can be scanned by the planar light fan.

33. An optical quality control system according to claim 31, wherein the light source transport system comprises an electrical drive and control system adapted to determine and control a position of the light source in the inspection direction.

34. The optical quality control system according to claim 19, wherein the optical inspection zone is adapted for inspection of the illuminated cross section in said inspection direction (A) essentially orthogonal to the plane (P).

35. The optical quality control system according to claim 19, wherein the container comprises a light absorbing surface portion arranged opposite the light source configured to reduce reflection of light within the container.

36. The optical quality control system according to claim 19, comprising an aperture or collimator configured to adjust the thickness of the planar light fan, measured in a direction orthogonal to the plane (P) defined by the planar illuminated cross-section.

37. The optical quality control system according to claim 19, comprising a support structure, wherein the optical inspection device is moveably connected to the support structure.

38. The optical quality control system according to claim 19, wherein the illuminated cross-section extends at least over the whole cross-section of the high refractive index solid.

* * * * *